US005684194A

United States Patent [19]

Pagani

[11] Patent Number: 5,684,194
[45] Date of Patent: Nov. 4, 1997

[54] PROCESS FOR UREA PRODUCTION INVOLVING A CARBON DIOXIDE STRIPPING STEP

[75] Inventor: Giorgio Pagani, Milan, Italy

[73] Assignee: Urea Casale S.A., Lugano, Switzerland

[21] Appl. No.: 482,560

[22] Filed: Jun. 7, 1995

Related U.S. Application Data

[62] Division of Ser. No. 178,749, Jan. 7, 1994, abandoned.

[30] Foreign Application Priority Data

Jan. 7, 1993 [CH] Switzerland ............... 00 048/93

[51] Int. Cl.⁶ ................................ C07C 273/04
[52] U.S. Cl. .......................... 564/67; 564/70
[58] Field of Search ........................ 564/67, 70

[56] References Cited

U.S. PATENT DOCUMENTS

| 4,504,679 | 3/1985 | Inou et al. ............... 564/67 |
|---|---|---|
| 4,613,696 | 9/1986 | Zardi ..................... 564/67 |
| 5,359,140 | 10/1994 | Granelli et al. ........... 564/67 |

FOREIGN PATENT DOCUMENTS

| 0479103 | 4/1992 | European Pat. Off. |
|---|---|---|
| 0497215 | 8/1992 | European Pat. Off. |

*Primary Examiner*—Shailendra Kumar
*Attorney, Agent, or Firm*—Sughrue, Mion, Zinn, Macpeak & Seas

[57] ABSTRACT

An improved process for urea production as well as a method of retrofitting a pre-existing urea plant based on the Stamicarbon process are disclosed. According to the invention, a high-yield reactor with partial removal of the reaction heat and a urea recovery section of the solution leaving the high-yield reactor, are added to the pre-existing urea plant, means being provided for recycling unreacted ammonia and carbon dioxide vapors as well as a carbamate solution obtained in the urea recovery section to the pre-existing reactor.

7 Claims, 3 Drawing Sheets

PROCESS FOR UREA PRODUCTION INVOLVING A CARBON DIOXIDE STRIPPING STEP

This is a divisional of application Ser. No. 08/178,749 filed Jan. 7, 1994, now abandoned.

DESCRIPTION

1. Field of Application

The present invention relates to an improved process for urea production, as well as to a method for retrofitting pre-existing urea production plants in which a reaction mixture leaving an urea synthesis reactor is submitted to a stripping step with carbon dioxide (Stamicarbon process).

The invention also relates to a plant for implementing the above mentioned process.

2. Background Art

As is well known, the need often arise of increasing the urea production capacity of a pre-existing plant.

To this end, various methods of enhancing the production capacity have been proposed heretofore, such as that described in European Patent application EP-A-0 479 103 by the same Applicant.

EP-A-0 479 103 discloses a process wherein highly pure ammonia and carbon dioxide are reacted in a first high-yield "once-through" reactor, the reaction mixture thus obtained is fed to a recovery section and a synthesis reaction between less pure reagents, substantially recycled from the recovery section (recovery mixture), is carried out in the pre-existing reactor of conventional type.

In copending U.S. application Ser. No. 08/059,241 by the same Applicant, the problem of increasing the urea production capacity and reducing energy consumptions in pre-existing plants according to the Stamicarbon Process (STC), i.e. including a $CO_2$ stripping section, is addressed by carrying out urea synthesis in the first high-yield reactor in adiabatic conditions (in a so-called "Vulcan" reactor) and by distilling the reaction mixture leaving the Vulcan reactor so as to obtain unreacted ammonia and carbamate streams recycled respectively to the Vulcan reactor itself and to the pre-existing low-yield reactor.

The process thus achieved appeared to-date to be satisfactory and further improvements did not seem to be possible.

Continuing his research and experiments, however, the Applicant was able to develop a new perfected revamping process applicable to the existing plants based on the total recycle process, with the aim of notably increasing the urea production capacity and reducing the energy consumption.

The aim of the present invention, therefore, is that of providing an improved process of producing urea which allows to obtain high conversion yields, a reduction of investment and operation costs, better plant exploitation and more ample overload margins of the existing equipment, and considerable plant debottlenecking.

SUMMARY OF THE INVENTION

This aim is accomplished, according to the invention, by a process of producing urea comprising the steps of:
  reacting ammonia and carbon dioxide in a first reaction space;
  effecting a gas stripping with carbon dioxide of a first reaction mixture leaving said first reaction space, so as to obtain a purified urea solution and unreacted ammonia and carbon dioxide vapors;
  feeding said purified urea solution to a first urea recovery section;
  condensing at a predetermined pressure said unreacted ammonia and carbon dioxide vapors in a carbamate condenser;
  reacting ammonia and carbon dioxide in a second reaction space;
wherein the method further comprises the steps of:
  a) submitting a second reaction mixture leaving said second reaction space to a first carbamate decomposition treatment at a pressure substantially equal to the pressure of the carbamate condenser, so as to separate a first stream of unreacted ammonia and carbon dioxide vapors from a liquid stream including urea;
  b) recycling the first stream of unreacted ammonia and carbon dioxide vapors to said carbamate condenser;
  c) submitting the liquid stream including urea to a second carbamate decomposition treatment so as to separate a second stream of unreacted ammonia and carbon dioxide vapors from a purified urea solution;
  d) condensing said second stream of unreacted ammonia and carbon dioxide vapors and recycling the condensate thus obtained to said carbamate condenser.

Urea synthesis in the first reaction space may be carried out at process conditions currently used in STC plants, such as—for example—at pressures of from 130 to 200 bar and temperatures of from 180 to 200° C.

The carbamate condensing step, the $CO_2$-stripping step of the reaction mixture leaving said reaction space and the urea recovery step in said recovery section, may also be carried out according to the known process conditions used in a STC plant.

Preferably, the urea synthesis in the second reaction space is carried out in a high-yield "once through" reactor, at pressures of from 240 to 260 bar and at temperatures of from 190 to 200° C.

A "once through" reactor with partial reaction heat removal has been observed to be particularly suitable for revamping urea production plants involving a $CO_2$ stripping step.

Most preferably, the "once through" reactor comprises two parts: a primary section with reaction heat removal and a secondary section of conventional type.

For the purposes of the present invention, particular advantages in terms of energy recovery are achieved when the "primary reactor" is of the so-called "Kettle" type.

According to the invention, the reaction mixture leaving the high-yield reaction space is submitted to a carbamate decomposition treatment so as to separate unreacted ammonia and carbon dioxide vapors from a liquid stream including urea.

More particularly, this reaction mixture is submitted to two carbamate decomposition treatments in series.

The first carbamate decomposition treatment is carried out in a high pressure decomposer at a pressure substantially equal to the pressure existing in a carbamate condenser provided upstream of the first reaction space.

Preferably, such a pressure ranges from from 140 to 150 bar.

Most advantageously, a first stream of unreacted ammonia and carbon dioxide vapors is obtained which may be directly recycled to the aforementioned carbamate condenser and further reacted in the first reaction space.

The second carbamate decomposition treatment of the solution leaving the first carbamate decomposer is carried out in a second carbamate decomposer at a pressure of from 6 to 18 bar, most preferably from 8 to 14 bar.

In this way, a second stream of unreacted ammonia and carbon dioxide vapors is obtained which is first condensed with the aid of an aqueous carbamate solution leaving the urea recovery section, and then recycled to the carbamate condenser as well.

The second carbamate decomposition treatment also yields a purified urea solution which may be either fed to a low-pressure distiller of the urea recovery section, or collected in a tank downstream of the low-pressure distiller before the finishing treatments in a vacuum section.

Advantageously, the carbon dioxide/urea molar ratio in the stripping treatment may be adjusted within optimal values by feeding up to 20% of the reaction mixture flow leaving the first urea synthesis reactor to the first carbamate decomposition treatment.

Preferably, from 10 to 15% of the reaction mixture flow leaving the first urea synthesis reactor by-passes the the $CO_2$ stripping treatment and is directly fed to the first carbamate decomposition treatment.

According to a further aspect of the present invention, it has been found after intensive studies and research that it is surprisingly possible to enhance in a simple and safe way the production capacity of a pre-existing urea production plant including a $CO_2$ stripping step.

When a capacity increase of over 20% of a pre-existing plant is required, it is advantageously possible to apply the concept of High Efficiency Parallel Reactor in order to accomplish the desired object of achieving a reduction of investment and operation costs, better plant exploitation and more ample overload margins of the existing equipment, and considerable plant debottlenecking.

The application of such concept to a pre-existing plant for urea production including:

a urea synthesis reactor;

a carbamate condenser upstream of said urea synthesis reactor;

a carbon dioxide stripper downstream of said urea synthesis reactor;

means for feeding a first reaction mixture leaving said first reactor to the carbon dioxide stripper;

a urea recovery section for separating urea from the first reaction mixture leaving the carbon dioxide stripper;

is carried out, in accordance with the invention, by a method of retrofitting comprising the steps of:

a) providing a second urea synthesis reactor connected with means for feeding high purity ammonia and carbon dioxide;

b) providing a second urea recovery section including at least a first and a second carbamate decomposers in series downstream of said second urea synthesis reactor;

c) providing conduit means for recycling unreacted ammonia and carbon dioxide vapors leaving the top of said first carbamate decomposer to said carbamate condenser;

d) providing means for condensing unreacted ammonia and carbon dioxide vapors leaving the top of said second carbamate decomposer;

e) providing means for recycling the condensate thus obtained to said carbamate condenser.

More particularly, of from 30 to 50% of the new requested production capacity is obtained in an additional high yield reactor (75%) of the "once through" type without recycle.

Most preferably, said reactor operates with partial removal of the reaction heat and comprises two parts: a primary section with reaction heat removal and a secondary section of conventional type.

Further aspects and advantages of the invention will be better apparent from the following description of preferred, though non-limitative, embodiments thereof carried out hereinbelow referring to the attached drawings.

DETAILED DESCRIPTION OF THE PREFERRED EMBODIMENTS

Figure 1:
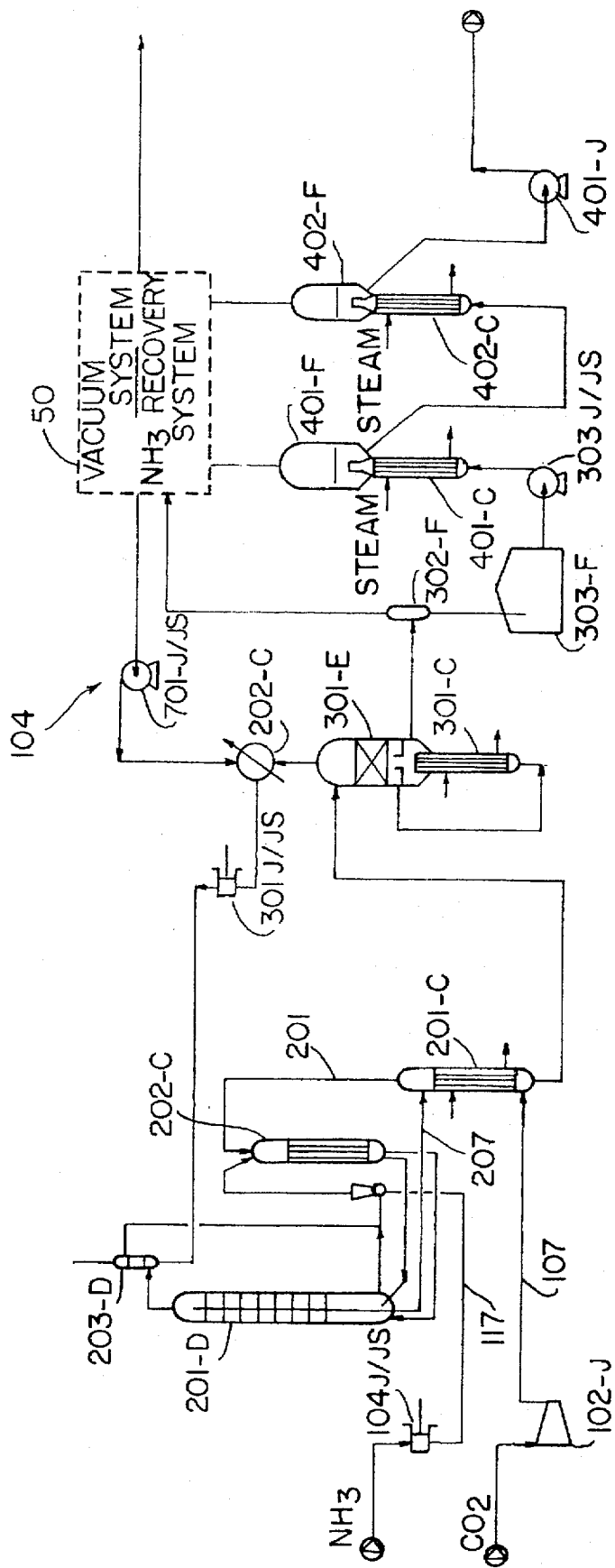
FIG. 1 shows a schematic layout of a urea production plant including a stripping step with $CO_2$ according to the prior art.

The urea production plant shown in FIG. 1 comprises a urea synthesis reactor 201-D to which pure ammonia ($NH_3$) and carbon dioxide ($CO_2$) are fed by conventional compressor means 104-J/JS and 102-J.

More particularly, ammonia is first fed to a carbamate condenser 202-C by conduit means 117, while carbon dioxide is fed to a stripper 201-C by conduit means 107 and then to the carbamate condenser 202-C by conduit means 201 before entering the urea synthesis reactor 201-D.

The stripper 201-C is also fed by the reaction mixture leaving the urea synthesis reactor 201-D through conduit 207.

With 104 is indicated a conventional urea recovery section, comprising a low-pressure distiller 301-C with relevant separator 301-E, two vacuum evaporators 401-C and 402-C with relevant separators 401-F and 402-F, as well as an ammonia vacuum concentration section 50.

The features of the urea recovery section 104 are per se conventional and well known in the art and will not be further described in detail.

In operation, a large part of the carbamate and part of the ammonia contained in the urea solution leaving the reactor 201-D are stripped in 201-C and recycled to the reactor, while a urea solution leaving the stripper 201-C is obtained having a relatively low $CO_2$ (7÷9% weight) and $NH_3$ (5÷8% weight) residues.

This solution is treated in the urea recovery section 104 where it is distilled at 3÷4 bar abs in 301-C: the vapors thus obtained are sent to condenser 302-C yielding a carbamate solution which is recycled to the urea synthesis reactor 201-D by means of pump 301-J/JS.

The main technical characteristics of the isobaric stripping process with $CO_2$ can be summarized as follows:

synthesis pressure: about 140÷145 bar abs

NH3/CO2 mol in the reactor: about 2.8÷3.0

H2O/CO2 mol in the reactor: about 0.4÷0.5 temperature of the reactor: about 185° C.

yield: about 57÷58% steam consumption: about 900÷1000 kg/MT urea

Figure 2:
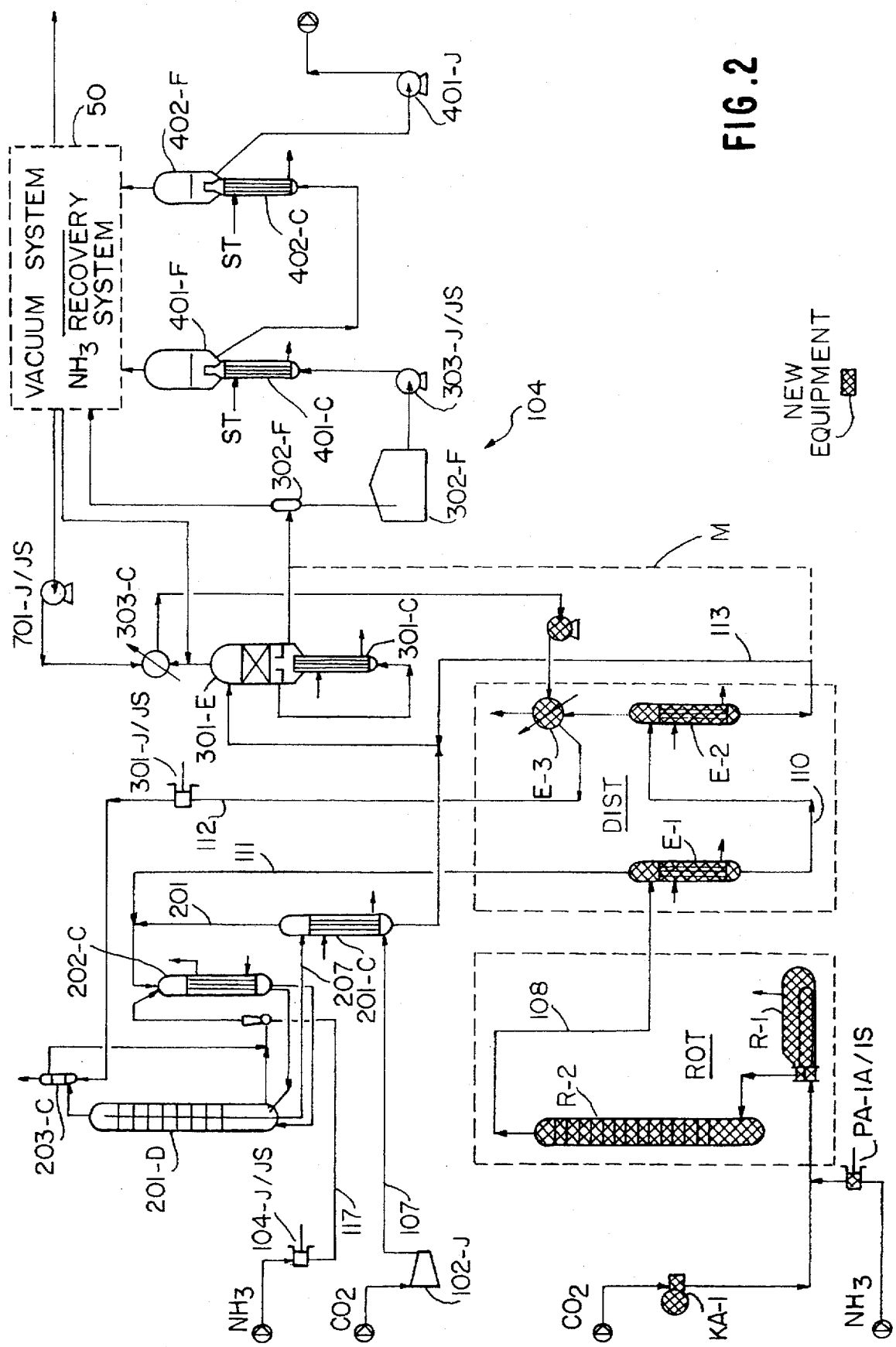
FIG. 2 shows a schematic layout of the urea production plant of FIG. 1 retrofitted in accordance with a first embodiment of the present invention.

According to a first embodiment of the present invention shown in FIG. 2, a high efficiency reactor ROT and a urea recovery section DIST for purifying a urea solution leaving the latter, are connected in parallel to the preexisting urea synthesis reactor 201-D.

The reactor ROT is fed by highly pure carbon dioxide by means of compressor means KA-1 and highly pure ammonia by pump means PA-1A/1S and is connected to the urea recovery section DIST through conduit 108.

Advantageously, the reactor ROT is of the "once-through" high yield type with partial removal of the reaction heat.

The "once through" reactor ROT comprises two parts: a primary section R-1 of the so-called "Kettle" type with reaction heat removal and a secondary section R-2 of conventional type.

The urea recovery section DIST preferably comprises at least two carbamate decomposers E-1 and E-2 connected in series through conduit means 110.

Most advantageously, the first carbamate decomposer E-1 operates at a pressure substantially equal to that of the existing stripper 201-C, while the second carbamate decomposer E-2 operates at approximately 10 bar abs.

According to an aspect of the present invention, a first stream leaving carbamate decomposer E-1, including unreacted ammonia and carbon dioxide vapors, is directly recycled to the carbamate condenser 202-C, operating at the same pressure, through conduit 111.

A second stream including unreacted ammonia and carbon dioxide vapors, which leaves the top of carbamate decomposer E-2, is first condensed in E-3 and then recycled to the carbamate condenser 202-C through conduit means 112 and pump 301-J/JS.

From the bottom of carbamate decomposer E-2 a purified urea solution is obtained, which may be either fed through conduit 113 to the low-pressure distiller 301-C of the urea recovery section 104, or directly collected to storage tank 302-F trough conduit M.

In the first instance, the urea solution leaving the carbamate decomposer E-2 is further treated together with the urea solution leaving the stripper 201-C in the low-pressure distiller 301-C.

Figure 3:
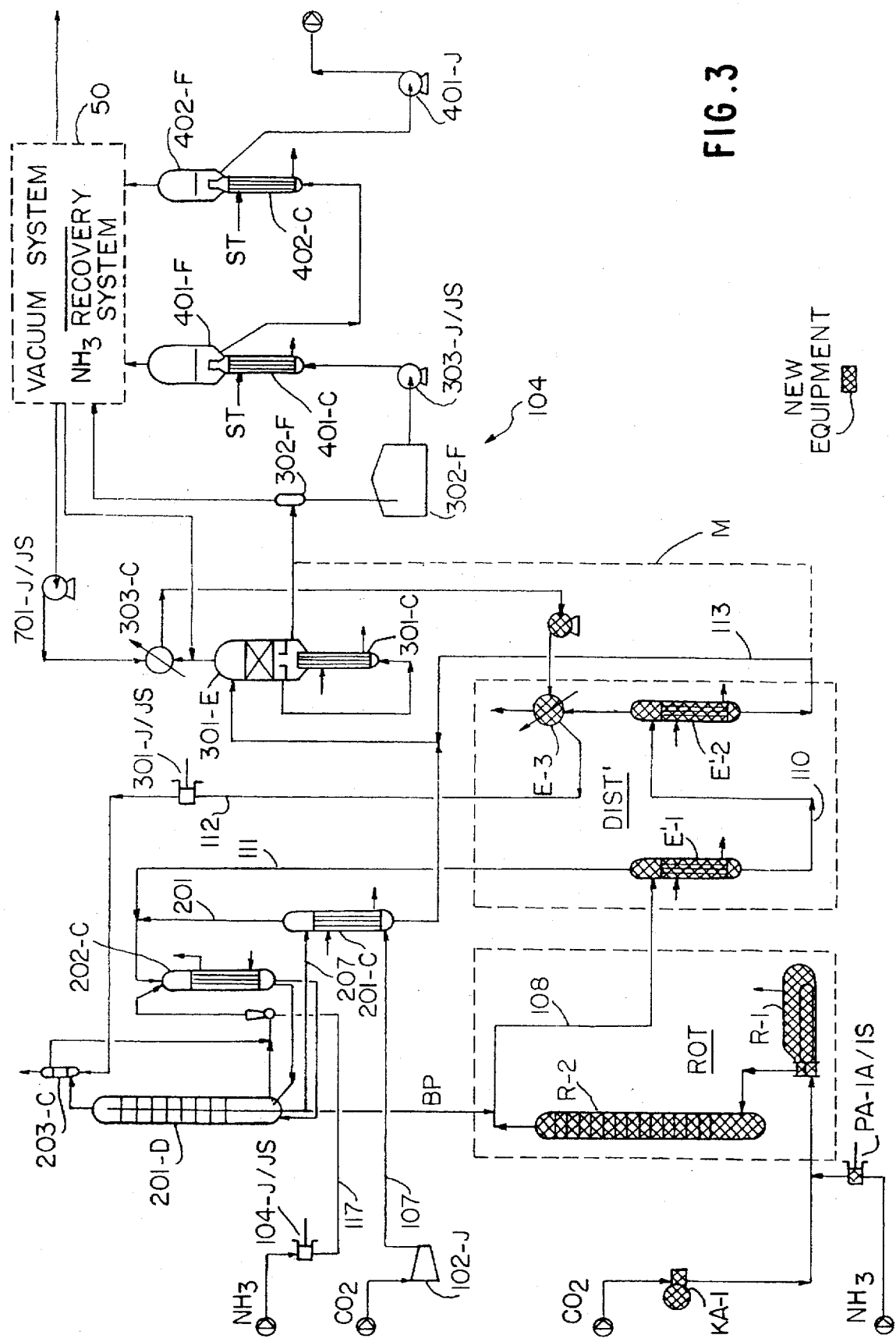
FIG. 3 shows a schematic layout of the urea production plant of FIG. 1 retrofitted in accordance with a second embodiment of the present invention.

According to a second embodiment of the present invention shown in FIG. 3, the pre-existing urea synthesis reactor 201-D is connected, through by-pass line BP to urea recovery section DIST' which in this case includes two carbamate decomposers E'-1, E'-2 designed so as to withstand the new load.

In this embodiment as well, the purified urea solution leaving column E'-2 may be either fed to the low-pressure distiller 301-C, or by-pass the same and and be directly collected into storage tank 302-F.

Further features and advantages of the invention, will be apparent from the non-limitative examples given hereinbelow, wherein revamping of an existing 1500 MT urea production plant with $CO_2$ stripping is illustrated.

EXAMPLE 1

The aim of the revamping is to increase the production capacity of a pre-existing plant from 1500 MTD to 2250 MTD, by adding a new reactor of the "once through" type in parallel to the existing one.

In the case herein considered, the optimal capacity distribution is as follows:

| existing reactor: | 1500 MTD urea |
|---|---|
| new reactor: | 750 MTD urea |
| Total: | 2250 MTD urea |

The operating conditions of the reactors are:
a) Reference Case
  Existing reactor (201-D):
  Capacity: 1500 MTD
  NH3/CO2 mol: 2.85
  H2O/CO2 mol: 0.40
  Yield : 57%
  P: 140 bar abs
  T: 183° C.
b) New Conditions
  b.1 Existing reactor (201-D):
  Capacity: 1500 MTD
  NH3/CO2 mol: 3.0
  H2O/CO2 mol: 0.53
  Yield: 57%
  P: 145 bar abs
  T: 185° C.
  b.2 New reactor (ROT):
  Capacity: 750 MTD
  NH3/CO2 mol: 3.6
  H2O/CO2 mol: 0
  Yield: 75%
  P: 242 bar abs
  T: 193° C.

The average weighed yield of the two reactors operating in parallel is:

$$\frac{1500 \times 57 + 750 \times 75}{2250} = 63\%$$

i.e. 6 points percent more than the reference case.

This corresponds to a lower specific steam consumption of 120+150 kg/MT urea, despite the capacity increase.

EXAMPLE 2

In Example 1, the capacity of the existing reactor in the new operating conditions was 1500 MTD of urea, i.e. equal to the design.

The existing stripper in this case will have at disposal for the urea solution stripping a lower quantity of $CO_2$ gas than the design (about 83% of the design), the balance will be as carbamate solution.

This lower quantity of $CO_2$ is anyway sufficient to achieve a good performance in the stripper 201-C.

In any case, it is possible to approach or substaantially reach the design carbon dioxide/urea ratio in the stripper 201-C, by operating according to the embodiment shown in FIG. 3.

The mentioned design ratio is achieved in this case by feeding about 17% of the reaction mixture flow leaving the pre-existing reactor 201-D to the carbamate decomposer E'-1 by-passing the stripper 201-C.

This aliqout of the reaction mixture is sent, through line BP, to the carbamate decomposer E'-1 of the new urea recovery section DIST', for the carbamate decomposition treatment.

Thanks to this by-pass, all the existing synthesis, stripping and urea recovery sections will work very close to or substantially within design conditions, avoiding any critical overload of these sections.

I claim:

1. A process of producing urea comprising the steps of:

reacting ammonia and carbon dioxide in a first reaction space;

effecting a gas stripping with carbon dioxide of a first reaction mixture leaving said first reaction space, so as to obtain a purified urea solution and unreacted ammonia and carbon dioxide vapors;

feeding said purified urea solution to a first urea recovery section;

condensing at a predetermined pressure said unreacted ammonia and carbon dioxide vapors in a carbamate condenser;

reacting ammonia and carbon dioxide in a second reaction space;

wherein the method further comprises the steps of:

a) submitting a second reaction mixture leaving said second reaction space to a first carbamate decomposition treatment at a pressure substantially equal to the pressure of the carbamate condenser, so as to separate a first stream of unreacted ammonia and carbon dioxide vapors from a liquid stream including urea;

b) recycling the first stream of unreacted ammonia and carbon dioxide vapors to said carbamate condenser;

c) submitting the liquid stream including urea to a second carbamate decomposition treatment so as to separate a second stream of unreacted ammonia and carbon dioxide vapors from a purified urea solution;

d) condensing said second stream of unreacted ammonia and carbon dioxide vapors and recycling the condensate thus obtained to said carbamate condenser.

2. A process according to claim 1, wherein said first carbamate decomposition treatment is carried out at a pressure of from 140 to 150 bar.

3. A process according to claim 1, wherein said second carbamate decomposition treatment is carried out at a pressure of from 6 to 18 bar.

4. A process according to claim 1, wherein urea synthesis in the second reaction space is carried out at pressures of from 240 to 260 bar and at temperatures of from 190 to 200° C. by means of a high-yield "once-through" reactor with partial removal of the reaction heat.

5. A process according to claim 1, further comprising the step of feeding the purified urea solution obtained from said second carbamate decomposition treatment to a low-pressure distiller of said urea recovery section.

6. A process according to claim 5, wherein the purified urea solution obtained from said second carbamate decomposition treatment is fed downstream of a low-pressure distiller of said urea recovery section.

7. A process according to claim 1, further comprising the step of subjecting part of the first reaction mixture leaving said first reaction space to said first and second carbamate decomposition treatments.

* * * * *